(12) United States Patent
Ashtekar et al.

(10) Patent No.: US 7,087,705 B2
(45) Date of Patent: Aug. 8, 2006

(54) PROCESS FOR THE MONOALKYLATION OF DIHYDROXY AROMATIC COMPOUNDS

(75) Inventors: Sunil Ashtekar, Bangalore (IN); Pramod Kumbhar, Mumbai (IN); Rathinam Jothi Mahalingam, Karnataka (IN); Jegadeesh Thampi, Karnataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/815,879

(22) Filed: Mar. 31, 2004

(65) Prior Publication Data

US 2005/0222372 A1   Oct. 6, 2005

(51) Int. Cl.
   *C08G 65/38* (2006.01)
(52) U.S. Cl. .............. 528/219; 502/303; 568/804
(58) Field of Classification Search .......... 502/303; 528/219; 568/804
   See application file for complete search history.

(56) References Cited

U.S. PATENT DOCUMENTS

| | | |
|---|---|---|
| 3,306,874 A | 2/1967 | Hay |
| 3,306,875 A | 2/1967 | Hay |
| 3,446,856 A | 5/1969 | Hamilton, Jr. |
| 3,707,569 A | 12/1972 | van Sorge et al. |
| 3,764,630 A | 10/1973 | van Sorge |
| 3,790,641 A | 2/1974 | Oshima et al. |
| 3,843,606 A | 10/1974 | van Sorge |
| 3,873,628 A | 3/1975 | Van Sorge |
| 3,953,529 A | 4/1976 | Yonemitsu et al. |
| 3,962,181 A | 6/1976 | Sakauchi et al. |
| 3,968,172 A | 7/1976 | Ichikawa et al. |
| 3,972,828 A | 8/1976 | van Sorge |
| 3,972,836 A | 8/1976 | van Sorge |
| 3,974,229 A | 8/1976 | van Sorge |
| 3,979,464 A | 9/1976 | Leach |
| 3,994,982 A | 11/1976 | Leach |
| 4,022,715 A | 5/1977 | Bornfriend |
| 4,022,843 A | 5/1977 | Leach |
| 4,024,195 A | 5/1977 | Yonemitsu et al. |
| 4,041,085 A | 8/1977 | Frabetti, Jr. |
| 4,048,239 A | 9/1977 | Smith |
| 4,083,828 A | 4/1978 | Olander |
| 4,085,150 A | 4/1978 | Smith |
| 4,092,294 A | 5/1978 | Bennett, Jr. et al. |
| 4,097,411 A | 6/1978 | Van Sorge |
| 4,097,441 A | 6/1978 | Sircar et al. |
| 4,126,750 A | 11/1978 | Poe et al. |
| 4,128,728 A | 12/1978 | Arnold et al. |
| 4,140,773 A | 2/1979 | Stowell et al. |
| 4,165,439 A | 8/1979 | Smith |
| 4,179,411 A | 12/1979 | Broersma et al. |
| 4,201,880 A | 5/1980 | van Sorge |
| 4,208,537 A | 6/1980 | Kawamata et al. |
| 4,215,229 A | 7/1980 | Greco |
| 4,227,023 A | 10/1980 | Kawamata et al. |
| 4,227,024 A | 10/1980 | Leach |
| 4,269,735 A | 5/1981 | Leach |
| 4,283,574 A | 8/1981 | Leach |
| 4,290,924 A | 9/1981 | Leach |
| 4,322,566 A | 3/1982 | Leach |
| 4,323,714 A | 4/1982 | Malloy et al. |
| 4,329,517 A | 5/1982 | Taniguchi et al. |
| 4,351,958 A | 9/1982 | Takahata et al. |
| 4,361,709 A | 11/1982 | Kawamata et al. |
| 4,375,566 A | 3/1983 | Kawamata et al. |
| 4,386,226 A | 5/1983 | Adey et al. |
| 4,418,224 A | 11/1983 | Bennett et al. |
| 4,454,357 A | 6/1984 | Inoue et al. |
| 4,458,031 A | 7/1984 | Battista et al. |
| 4,460,702 A | 7/1984 | Smith |
| 4,469,908 A | 9/1984 | Burress |
| 4,471,149 A | 9/1984 | Adey et al. |
| 4,475,001 A | 10/1984 | Leston |
| 4,476,329 A | 10/1984 | Chambers et al. |
| 4,482,758 A | 11/1984 | Seig |
| 4,517,389 A | 5/1985 | Katsumata et al. |
| 4,528,407 A | 7/1985 | Smith et al. |
| 4,533,650 A | 8/1985 | Courty et al. |
| 4,547,480 A | 10/1985 | Bennett, Jr. et al. |
| 4,554,266 A | 11/1985 | Bennett et al. |
| 4,554,267 A | 11/1985 | Chambers et al. |
| 4,560,810 A | 12/1985 | Talley et al. |
| 4,572,778 A | 2/1986 | Ward |
| 4,590,307 A | 5/1986 | Bennett, Jr. et al. |
| 4,605,766 A | 8/1986 | Hargis |
| 4,612,362 A | 9/1986 | Lai et al. .............. 528/190 |
| 4,644,086 A * | 2/1987 | Voges et al. ............ 568/804 |
| 4,661,638 A * | 4/1987 | Battista et al. .......... 568/804 |
| 4,677,089 A | 6/1987 | Bennett, Jr. et al. |
| 4,720,478 A | 1/1988 | Voges et al. |

(Continued)

FOREIGN PATENT DOCUMENTS

EP     0 102 493     3/1984

(Continued)

OTHER PUBLICATIONS

International Search Report for PCT/US02/31654, mailed Jan. 28, 2003.

(Continued)

Primary Examiner—Terressa Boykin

(57) ABSTRACT

A continuous process comprising: contacting a mixture comprising dihydroxy aromatic compound, water and an alkylating agent with a catalyst system in the presence of a flowing carrier gas, to form a mono alkylated dihydroxy aromatic compound, wherein the catalyst system is obtained by the calcination of a catalyst precursor system comprising a metal oxide precursor, a transition metal element and a pore former.

27 Claims, No Drawings

U.S. PATENT DOCUMENTS

| | | |
|---|---|---|
| 4,753,913 A | 6/1988 | Lenz et al. |
| 4,814,083 A | 3/1989 | Ford et al. |
| 4,822,836 A | 4/1989 | Wroczynski |
| 4,851,591 A | 7/1989 | Battista et al. |
| 4,874,810 A | 10/1989 | Lee, Jr. et al. |
| 4,876,398 A | 10/1989 | Lin et al. |
| 4,900,708 A | 2/1990 | Bennett et al. |
| 4,912,264 A | 3/1990 | Takeshita et al. |
| 4,933,509 A | 6/1990 | Warner |
| 4,954,475 A | 9/1990 | Bennett, Jr. et al. |
| 4,969,989 A | 11/1990 | Simpson |
| 5,017,655 A | 5/1991 | Kase et al. |
| 5,017,656 A | 5/1991 | Bopp |
| 5,059,727 A | 10/1991 | Ito |
| 5,097,079 A | 3/1992 | Bennett, Jr. et al. |
| 5,128,304 A | 7/1992 | Ito |
| 5,132,468 A | 7/1992 | Doussain et al. |
| 5,175,375 A | 12/1992 | Chang et al. |
| 5,227,342 A | 7/1993 | Anderson et al. |
| 5,245,089 A | 9/1993 | Irick, Jr. et al. |
| 5,321,105 A | 6/1994 | Rekers et al. |
| 5,345,005 A | 9/1994 | Thakur et al. |
| 5,371,306 A | 12/1994 | Woo et al. |
| 5,434,326 A | 7/1995 | Gajda et al. ............. 585/467 |
| 5,488,173 A | 1/1996 | Wang |
| 5,622,684 A | 4/1997 | Pinnavaia et al. |
| 5,672,558 A | 9/1997 | White et al. |
| 5,795,559 A | 8/1998 | Pinnavaia et al. |
| 5,840,271 A | 11/1998 | Carrazza et al. ............. 423/700 |
| 5,847,237 A | 12/1998 | Yago et al. |
| 5,874,374 A | 2/1999 | Ong ............. 501/12 |
| 5,986,138 A | 11/1999 | Satyavathi et al. |
| 5,998,317 A | 12/1999 | Sterzel ............. 501/80 |
| 6,037,295 A | 3/2000 | Satyavathi et al. |
| 6,049,008 A | 4/2000 | Roberts et al. |
| 6,054,627 A | 4/2000 | Thakur et al. |
| 6,153,547 A | 11/2000 | Sterzel ............. 501/80 |
| 6,187,981 B1 | 2/2001 | Marinangeli et al. |
| 6,203,774 B1 | 3/2001 | Han et al. |
| 6,261,987 B1 | 7/2001 | Watson et al. |
| 6,291,724 B1 | 9/2001 | Braat |
| 6,294,499 B1 | 9/2001 | Watson et al. |
| 6,303,801 B1 | 10/2001 | Suzuki et al. |
| 6,395,871 B1 | 5/2002 | Watson et al. |
| 6,448,458 B1 | 9/2002 | Marinangeli et al. |
| 2003/0073572 A1 | 4/2003 | Parrillo et al. |
| 2003/0125586 A1 | 7/2003 | Sankarasubbier et al. |
| 2003/0194366 A1* | 10/2003 | Srinivas et al. ............. 423/230 |
| 2005/0004407 A1* | 1/2005 | Ingelbrecht et al. ......... 568/794 |
| 2005/0009697 A1 | 1/2005 | Ingelbrecht et al. ......... 502/340 |

FOREIGN PATENT DOCUMENTS

| | | |
|---|---|---|
| EP | 0 129 065 B1 | 5/1984 |
| EP | 0 171 792 | 2/1986 |
| EP | 0 438 329 A1 | 7/1991 |
| EP | 0 785 180 A2 | 7/1997 |
| EP | 0 987 220 A1 | 3/2000 |
| EP | 1 041 061 B1 | 10/2003 |
| FR | 2 670 778 A1 | 6/1992 |
| WO | WO 84/01146 | 3/1984 |
| WO | WO 0138223 | 5/2001 |
| WO | WO 01/64334 | 9/2001 |

OTHER PUBLICATIONS

International Search Report for International Application No. PCT/US2005/010859 mailed Jul. 26, 2005.

Japanese Patent No. JP55115835, abstract only.

* cited by examiner

PROCESS FOR THE MONOALKYLATION OF DIHYDROXY AROMATIC COMPOUNDS

BACKGROUND OF INVENTION

The disclosure generally relates to alkylation of dihydroxy aromatic compounds. More particularly the disclosure relates to selective mono ortho alkylation of dihydroxy aromatic compounds.

An alkylation reaction of a dihydroxy aromatic compound typically involves a vapor phase reaction of a dihydroxy aromatic compound with an alcohol using an alkylation catalyst. Such alkylated dihydroxy aromatic compounds find applications in a wide range of industries including, among others, the polymer industry, the dye industry, the photographic industry and in medical applications. They are also known for fabricating polycarbonates for use in liquid crystal displays.

Many alkylation processes for hydroxy aromatic compounds use metal oxide catalysts. Many of the alkylating catalysts produce a mixture that often contains a high proportion of dialkylated hydroxy aromatic compounds with very low selectivities towards mono alkylated hydroxy aromatic compounds. Dihydroxy aromatic compounds tend to be more reactive than hydroxy aromatic compounds thereby having an even greater tendency to generate higher alkylated and oligomeric products and making the production of mono alkylated products more difficult.

Thus, there exists an ongoing need for improvement in the process for the preparation of mono alkylated dihydroxy aromatic compounds, particularly mono ortho-alkylated dihydroxy aromatic compounds.

SUMMARY OF INVENTION

A continuous process comprising:
contacting a mixture comprising dihydroxy aromatic compound, water and an alkylating agent with a catalyst system in the presence of a flowing carrier gas, to form a mono alkylated dihydroxy aromatic compound, wherein said catalyst system is obtained by the calcination of a catalyst precursor system comprising a metal oxide precursor, a transition metal element and a pore former.

The above-described method may be understood more readily by reference to the following detailed description of the various features of the disclosure and the examples included therein.

DETAILED DESCRIPTION

Disclosed herein is a process for mono alkylation of dihydroxy aromatic compounds providing a high degree of selectivity towards mono alkylation, particularly mono ortho alkylation. The process of mono alkylating a dihydroxy aromatic compound comprises contacting a reaction mixture comprising the dihydroxy aromatic compound, water and an alkylating agent with a catalyst system in the presence of a flowing carrier gas, at a weighted hourly space velocity, to form a mono alkylated dihydroxy aromatic compound, wherein said catalyst system is obtained by the calcination of a catalyst precursor system. The reaction mixture may further comprise a diluent. The catalyst precursor system comprises a metal oxide precursor, a transition metal and a pore former. After calcination the metal oxide precursor is converted to the metal oxide and the calcined catalyst may have pores with average pore diameters of 100 to 400 Angstroms.

The singular forms "a", "an" and "the" include plural referents unless the context clearly dictates otherwise. "Optional" or "optionally" means that the subsequently described event or circumstance may or may not occur, and that the description includes instances where the event occurs and instances where it does not. Whenever a range of values are given it should be understood that it includes all subranges contained therein.

Unless otherwise specified, the term "alkyl" as used herein is intended to designate straight chain alkyls and branched alkyls. The straight chain and branched alkyl groups include as illustrative non-limiting examples, methyl, ethyl, n-propyl, isopropyl, n-butyl, iso-butyl and tertiary-butyl groups.

The dihydroxy aromatic compounds may be selected from the group consisting of hydroquinone compounds, resorcinol compounds and catechol compounds. In one embodiment the dihydroxy aromatic compounds are of the formula:

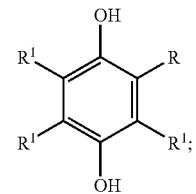

wherein R is a hydrogen group and each occurrence of $R^1$ is independently selected from the group consisting of a hydrogen and a hydrocarbyl group selected from the group consisting of an alkyl group containing 1 to 18 carbon atoms, an aryl group containing about 6 to 20 carbon atoms, an arylalkyl group containing about 7 to 12 carbon atoms and an alkylaryl group containing about 7 to 16 carbon atoms.

Specific examples of suitable dihydroxy aromatic compounds include hydroquinone, resorcinol, catechol, 2-methyl hydroquinone, 2,5-dimethyl hydroquinone, 2-ethyl hydroquinone, 2,5-diethyl hydroquinone, 2-tertiarybutyl hydroquinone 2,5-ditertiarybutyl hydroquinone, 2-phenyl hydroquinone, 2-benzyl hydroquinone, 2,3,5-trimethyl hydroquinone, 2-vinyl hydroquinone, 2-isopropyl hydroquinone, 2,5-diisopropyl hydroquinone, and mixtures of two or more of the foregoing dihydroxy aromatic compounds.

An alkylating agent is a reactant, which under the conditions described herein reacts with a dihydroxy aromatic compound to provide a mono alkylated dihydroxy aromatic compound. The alkylating agents used in the process may be selected from the group consisting of branched chain or straight chain alkyl alcohols containing 1 to 16 carbon atoms and branched chain or straight chain olefins containing 2 to 16 carbon atoms. Exemplary alkyl alcohols include methyl alcohol, ethyl alcohol, 2-propyl alcohol, isopropyl alcohol, n-butyl alcohol, isobutyl alcohol, amyl alcohol, isoamyl alcohol, hexyl alcohol, heptyl alcohol, octyl alcohol, nonyl alcohol, decyl alcohol, lauryl alcohol, cetyl alcohol, cyclohexyl alcohol, and cyclohexylmethyl alcohol. Exemplary olefins include ethylene, propylene, 1-butylene, 2-butylene, isobutylene, 1-pentene, 2-pentene, 2-methylpentene-2, 3-methylpentene-2, 1-hexene, 2-hexene, 3-hexene, 1-heptene, 2-heptene, 3-heptene, the isomeric octenes, nonenes and decenes. In one embodiment the alkylating agent is methanol. The molar ratio of the alkylating agent to the dihydroxy aromatic compound is 0.5 to 4 moles per mole of dihydroxy aromatic compound or, more specifically, the molar ratio is 1 to 3.5 moles per mole of dihydroxy aromatic compound, or, even more specifically, the molar ratio is 2 to 3 moles per mole of dihydroxy aromatic compound.

It is to be understood that the aforementioned dihydroxy aromatic compounds and alkylating agents are only representative of the class of compounds that may be employed.

Methods of preparing the catalysts systems described herein are disclosed in commonly assigned, co-pending U.S. patent application Ser. No. 10/065134. The catalyst system employed is obtained by the calcination of a catalyst precursor system comprising at least one metal oxide precursor, which is converted to a metal oxide during calcination, a promoter and a pore-former.

Metal oxide precursors include magnesium oxide precursors, iron oxide precursors, chromium oxide precursors, vanadium oxide precursors, copper oxide precursors, lanthanum oxide precursors and mixtures of two or more of the foregoing. The metal oxide precursor may comprise any metal reagent which yields the corresponding metal oxide under calcination conditions such as nitrates, carbonates, oxides, hydroxides, sulphates and mixtures of two or more of the foregoing. For example, any magnesium reagent which yields magnesium oxide after calcination can be used. In one embodiment the metal oxide precursor comprises magnesium hydroxide, magnesium nitrate, magnesium carbonate, magnesium sulphate, magnesium acetate or a mixture of two or more of the foregoing. In another embodiment the metal oxide precursor comprises magnesium carbonate.

The pore former used in the catalyst system is a substance capable of aiding the formation of pores in the catalyst. Under the calcination condition described herein the pore former decomposes or burns off leaving behind pores in the catalyst. The pore former may be selected from the group consisting of waxes and polysaccharides. Exemplary waxes include, but are not limited to, paraffin wax, polyethylene wax, microcrystalline wax, montan wax, and combinations of two or more of the foregoing. Exemplary polysaccharides may be cellulose, carboxyl methyl cellulose, cellulose acetate, starch, walnut powder, citric acid, polyethylene glycol, oxalic acid, stearic acid and combinations of two or more of the foregoing. Also useful are anionic and cationic surfactants, typically long chain ($C_{10-28}$) hydrocarbons containing neutralized acid species, e.g., carboxylic acid, phosphoric acid, and sulfonic acid species. In one embodiment the pore former is polyethylene glycol.

The amount of the pore former employed is that which provides for average pore diameters of 100 to 400 Angstroms (Å) after calcination. The amount of pore former may be 100 ppm to 10 wt %, or, more specifically, 100 ppm to about 5 weight percent, or, even more specifically, up to 2 weight percent with respect to catalyst precursor reagent. The pore former is typically blended with the metal oxide precursor and transition metal to provide uniform distribution of the pore former along with other components of the catalyst such as binders and fillers. Transition metal elements are used as promoters in the catalyst system. Specific examples of suitable transition metal elements include copper, chromium, zinc, cobalt, nickel, manganese and mixtures of two or more of the foregoing. In one embodiment the promoter is copper.

The catalyst precursor system is converted to the catalyst through calcination. In one embodiment gas, such as air, nitrogen, or a combination thereof, is passed through the catalyst precursor system during all or part of the calcination. The catalyst precursor system may be heated prior to calcination and heating may also occur with gas flow. It is believed that gas flow may aid in the formation of pores having the desired pore size.

Calcination is usually carried out by heating the catalyst at a temperature sufficient to convert the metal oxide precursor to the corresponding metal oxide. Useful calcination procedures are found in U.S. Pat. Nos. 6,294,499 and 4,554,267. The calcination temperature may vary somewhat, but is usually 350° C. to 600° C. Slow heating rates can lead to desirable larger pore sizes but often at the expense of lower activity of the resultant catalyst. Typically, the heating rate for commercial scale will be to raise the temperature from ambient to 400° C. over a 12 to 18 hour range although the exact rate can vary depending on the actual reactor size and geometry. The calcination atmosphere may be oxidizing, inert, or reducing. Alternatively, the catalyst can be calcined at the beginning of the alkylation reaction. In other words, calcination can take place in the presence of the alkylation feed materials, i.e., the dihydroxy aromatic compound and the alkyl alcohol. The surface area of the catalyst after calcination is usually 100 $m^2$/g to 250 $m^2$/g, based on grams of metal oxide.

In one embodiment the catalyst has, after calcination, a distribution of pores having an average size of 100 Å to 400 Å in diameter. The metal oxide alkylation catalyst may have a bimodal distribution of pores. In one embodiment the bimodal distribution of pores has a first distribution of pores wherein the first distribution has an average pore diameter less than 100 Angstroms and a second distribution of pores wherein the second distribution has an average diameter greater than 100 Angstroms and less than 400 Angstroms. Without being bound by theory it is believed that these large pores in the catalyst may reduce the retention time of the substrate, thereby increasing the mono-alkyl selectivity.

Without being bound by theory, it is believe that the presence of water in the reaction mixture helps to reduce coke formation. Water also serves as a diluent. The amount of water added is 1 mole to 10 moles per mole of the aromatic dihydroxy compound or, more specifically, 2 to 8 moles per mole of the aromatic dihydroxy compound, or, even more specifically, 3 to 5 moles per mole of the aromatic dihydroxy compound.

The reaction mixture comprising dihydroxy aromatic compound, water and alkylating agent can additionally comprise a diluent to facilitate the reaction. The diluents employed in the reaction are selected from the group consisting of solvents that vaporize or are in a vapor state at the temperatures of 300° C. to 500° C. and are stable and undergo little or no decomposition in this temperature range. Suitable examples of diluent include, but are not limited to, monoglyme, diglyme, triglyme, tetraglyme, butyl diglyme, glycol, polyglycol and dipropylene glycol dimethyl ether. In one embodiment the diluent is monoglyme. The amount of diluent used is 0.1 mole to 10 moles per mole of dihydroxy aromatic compound, or, more specifically, 1 to 8 moles per mole of dihydroxy aromatic compound, or, even more specifically, 1 to 2 moles per mole of dihydroxy aromatic compound.

The alkylation reaction occurs at a temperature of 300° C. to 500° C., or, more specifically, at a temperature of 400° C. to 500° C., or, even more specifically, at a temperature of 440° C. to 480° C.

Inert carrier gases that may be used in the alkylation process include, but are not limited to, nitrogen, hydrogen, helium, argon, carbon monoxide and mixtures of two or more of the foregoing gases. In one embodiment the carrier gas employed comprises nitrogen. The amount of carrier gas used is 1 mole to 12 moles per mole of dihydroxy aromatic compound, or, more specifically, 5 moles to 10 moles of dihydroxy aromatic compound, or, even more specifically, 6 moles to 8 moles per mole of dihydroxy aromatic compound.

The weighted hourly space velocity (WHSV) of the feed is 0.1 to 10, or, more specifically, 2 to 5, or, even more specifically, 1 to 3. The weighted hourly space velocity is the mass of feed per unit of catalyst per unit of time.

In an exemplary procedure a reactor is loaded with the catalyst precursor system prepared as given above. It is then calcined in-situ for about 22 hours at about 390° C. under an inert atmosphere of nitrogen gas, at atmospheric pressure. After calcination, the temperature is increased to about 400–500° C. over a period of two hours under an inert atmosphere of nitrogen gas. A premixed solution of the feed mixture comprising dihydroxy aromatic compound, alkylating agent, diluent and water, is introduced at a desired flow rate measured in terms of WHSV. Alternatively, in the absence of a diluent in the reaction, a first feed stream comprising dihydroxy aromatic compound in the molten state is added simultaneously with a second feed stream comprising water and alkylating agent.

The process described herein may have a selectivity for mono ortho alkylated products greater than or equal to 50%, or, more specifically, greater than or equal to 60%, or, even more specifically, greater than or equal to 70%. Selectivity is calculated as described below in the Examples.

As previously discussed, the mono alkylated dihydroxy aromatic compounds find various end use applications in the polymer, dyestuff, pharmaceutical, photographic industries and in medical applications. Polycarbonates particularly containing mono alkylated dihydroxy aromatic units are known to exhibit liquid crystalline properties. Suitable methods for preparation of these polycarbonates include melt-polymerization reaction of diphenylcarbonate and mixtures of dihydroxy compounds comprising mono alkylated dihydroxy aromatic compounds such as methyl hydroquinone in the presence of quaternary phosphonium salts, sodium hydroxide or tetraalkylammonium salts as catalyst systems. The mono alkylated dihydroxy aromatic compounds can also be used to prepare polyesters when coupled with other monomers by melt polymerization techniques as is known in the art.

The process is further described by the following non-limiting examples.

EXAMPLES

In the following examples and comparative examples, a high performance liquid chromatography (HPLC) method was used to quantify the conversion of a dihydroxy aromatic compound to a mono ortho-alkylated dihydroxy aromatic compound. The HPLC was initially calibrated using standard Aldrich samples of hydroquinone (HQ), and 2-methyl hydroquinone (2-Me HQ) and 2,6-dimethyl hydroquinone (2,6 di Me HQ). The standard samples were diluted with an internal standard solution of N-methyl benzamide in acetonitrile and injected into a C-18 reverse phase column. Each reaction mixture sample was diluted with an internal standard solution of N-methyl benzamide in acetonitrile and injected into a C-18 reverse phase column. Samples at specific time intervals were analyzed and compared to the HPLC chromatogram of the standard sample to determine the conversion of hydroquinone and selectivity towards formation of 2-methyl hydroquinone and 2,6-dimethyl hydroquinone.

Example: 1

A dry mixture of 100 grams (gms) of magnesium carbonate, 2.5 gms of polyethylene glycol, 1 gram (gm) graphite, and 1000 ppm of copper nitrate was prepared. This mixture was pelletized and crushed to particles having a size of 800–1400 micrometers to provide the catalyst precursor system.

Examples 2–10:

A glass reactor was loaded with 5 grams of the catalyst precursor system prepared in example 1. The catalyst was calcined in-situ for 22 hours at 390° C. under a flow of nitrogen, at atmospheric pressure. After calcination, the temperature was increased to 480° C. over a period of two hours under a nitrogen atmosphere. After 15 minutes, a feed mixture comprising hydroquinone, methanol (MeOH), monoglyme and water, was introduced at the flow rates indicated by the weighted hourly space velocity (WHSV) in Table 1. The molar ratio of hydroquinone to monoglyme to water was maintained at 1:2:3 and the carrier gas to hydroquinone molar ratio was maintained at 8:1. The temperature of the feed mixture and the molar ratio of methanol to hydroquinone were varied as indicated in Table 1. The alkylation was run for 24 hours under the above mentioned conditions during which methyl hydroquinone selectivity and dimethyl hydroquinone selectivity were monitored on HPLC. Samples for measuring conversion and selectivity were withdrawn as indicated by the time of sampling (TOS) data indicated in Table 1 below. 2-Methyl hydroquinone selectivity was calculated as follows: 2-MeHQ selectivity= (moles of 2-MeHQ formed/moles of HQ converted) *100%.

TABLE 1

| Ex. | HQ in moles | MeOH/HQ | Time of sampling in hours | WHSV | Temp in ° C. | HQ conversion in mole % | 2-MeHQ selectivity in mole % | 2,6-di Me HQ selectivity in mole % |
| --- | --- | --- | --- | --- | --- | --- | --- | --- |
| 1 | 1 | 3 | 10 | 1.3 | 480 | 25 | 75 | 13 |
| 2 | 1 | 2 | 10 | 1 | 480 | 50 | 32 | 20 |
| 3 | 1 | 3 | 10 | 1.3 | 465 | 27 | 53 | 15 |
| 4 | 1 | 4 | 10 | 1.6 | 480 | 30 | 55 | 26 |
| 5 | 1 | 2 | 10 | 1.6 | 480 | 24 | 63 | 10 |
| 6[1] | 1 | 3 | 10 | 1.3 | 480 | 38 | 44 | 17 |
| 7[2] | 1 | 3 | 24 | 1.3 | 480 | 15 | 64 | 13 |

TABLE 1-continued

| Ex. | HQ in moles | MeOH/HQ | Time of sampling in hours | WHSV | Temp in ° C. | HQ conversion in mole % | 2-MeHQ selectivity in mole % | 2,6-di Me HQ selectivity in mole % |
|---|---|---|---|---|---|---|---|---|

[1] Hydrogen as the carrier gas
[2] 5 moles of water per mole of hydroquinone.

These experiments indicate that the use of polyethylene glycol pore-former in the catalyst precursor system increases the selectivity towards 2-methyl hydroquinone. The presence of the pore former in the catalyst precursor provides larger pore sizes in the catalyst system on calcination. Without being bound by theory it is belived that the 2-methyl hydroquinone may diffuse out faster from the larger catalyst pores, thus reducing the over alkylation due to reduced contact time with the catalyst.

Comparative Example

A similar procedure was followed as in examples 2–10, except that the catalyst precursor contained only magnesium carbonate. Results are shown in Table 2.

TABLE 2

| Ex. | HQ in moles | MeOH/HQ | Time of sampling in hours | WHSV | Temp in ° C. | HQ conversion in mole % | 2-MeHQ selectivity in mole % | 2,6-di Me HQ selectivity in mole % |
|---|---|---|---|---|---|---|---|---|
| Comp Ex. 1 | 1 | 3 | 10 | 1.3 | 480 | 34 | 49 | 15 |

As can be seen by a comparison of Example 1 and Comparative Example 1 use of only magnesium carbonate as the catalyst precursor in the absence of a promoter and pore-former shows decreased selectivity towards 2-methyl hydroquinone under similar operating conditions.

The foregoing examples show that the use of a catalyst having pore size of 100 to 400 Å results in an alkylation process for dihydroxy aromatic compounds that has surprisingly high selectivity for mono alkylated products, particularly mono ortho alkylated products.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

All patents and patent applications cited herein are incorporated by reference.

The invention claimed is:

1. A continuous process comprising:
   contacting a mixture comprising a dihydroxy aromatic compound, water and an alkylating agent with a catalyst system in the presence of a flowing carrier gas, to form a mono alkylated dihydroxy aromatic compound, wherein said catalyst system is obtained by the calcination of a catalyst precursor system comprising a metal oxide precursor, a transition metal element and a pore former, wherein said pore former is selected from the group consisting of waxes and polysaccharides.

2. The process of claim 1, wherein said compound has a formula:

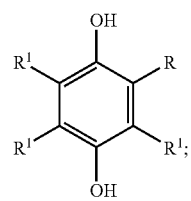

wherein R is hydrogen and each occurrence of $R^1$ is independently selected from the group consisting of hydrogen and a hydrocarbyl group selected from the group consisting of an alkyl group containing 1 to about 18 carbon atoms, an aryl group containing about 6 to about 20 carbon atoms, an arylalkyl group containing about 7 to about 12 carbon atoms and an alkylaryl group containing about 7 to about 16 carbon atoms.

3. The process of claim 1, wherein said dihydroxy aromatic compound is selected from the group consisting of hydroquinone, resorcinol, catechol, 2-methyl hydroquinone, 2,5-dimethyl hydroquinone, 2-ethyl hydroquinone, 2,5-diethyl hydroquinone, 2-tertiarybutyl) hydroquinone 2,5-ditertiarybutyl hydroquinone, 2-phenyl hydroquinone, 2-benzyl hydroquinone, 2,3,5-trimethyl hydroquinone, 2-vinyl hydroquinone, 2-isopropyl hydroquinone, 2,5-diisopyl hydroquinone, and mixtures of two or more of the foregoing dihydroxy aromatic compound.

4. The process of claim 1, wherein said dihydroxy aromatic compound comprises hydroquinone.

5. The process of claim 1, wherein said alkylating agent is selected from a group consisting of branched chain or straight chain alkyl alcohols containing 1 to 16 carbon atoms and branched chain or straight chain olefins containing 2 to 16 carbon atoms.

6. The process of claim 1, wherein said alkylating agent is selected from a group consisting of methyl alcohol, ethyl alcohol, n-propyl alcohol, isopropyl alcohol, n-butyl alcohol, isobutyl alcohol, amyl alcohol, isoamyl alcohol hexyl alcohol, heptyl alcohol, octyl alcohol, nonyl alcohol, decyl alcohol, lauryl alcohol, cetyl alcohol, cyclohexyl alcohol, cyclohexylmethyl alcohol, ethylene, propylene, 1-butylene, 2-butylene, isobutylene, 1-pentene, 2-pentene, 2-methylpentene-2, 3-methylpentene-2, 1-hexene, 2-hexene, 3-hexene, 1-heptene, 2-heptene, 3-heptene, the isomeric octenes, nonenes and decenes.

7. The process of claim 1, wherein n said alkylating agent comprises methyl alcohol.

8. The process of claim 1, wherein said metal oxide precursor is selected front a group consisting of magnesium oxide precursor, iron oxide precursor, chromium oxide precursor, vanadium oxide precursor, copper oxide precursor, lanthanum oxide precursor and mixtures of two or more of the foregoing.

9. The process of claim 1, wherein said metal oxide precursor comprises a magnesium oxide precursor.

10. The process of claim 1, wherein said metal oxide precursor comprises magnesium carbonate.

11. The process of claim 1, wherein said transition metal element comprises copper.

12. The method of claim 1, wherein the pore former comprises polyethylene glycol.

13. The process of claim 1, wherein said contacting is carried out at a weighed hourly space velocity of 0.1 to 10.

14. The process of claim 1, wherein the molar ratio of alkylating agent to dihydroxy aromatic compound is 0.5 to 4.

15. The process of claim 1, wherein the carrier gas is selected from a group consisting of nitrogen, hydrogen, helium, argon, carbon monoxide and mixtures of two or more of the foregoing gases.

16. The process of claim 1, wherein mono alkylation of the dihydroxy aromatic compound is carried out at a temperature of 300° C. to 500° C.

17. The process of claim 1, wherein the mixture further comprises a diluent.

18. The process of claim 17, wherein the diluent is selected from a group consisting of monoglyme, diglyme, triglyme, tetraglyme, butyl diglyme, glycol, polyglycol and dipropylene glycol dimethyl ether.

19. The process of claim 17, wherein the diluent is monoglyme.

20. The process of claim 17, wherein the molar ratio of diluent to dihydroxy aromatic compound is about 0.1 to about 10.

21. The process of claim 1, wherein the catalyst has pores having pore diameters of 100 to 400 Angstroms.

22. A continuous process comprising:
    contacting a mixture comprising a dihydroxy aromatic compound, water and an alkylating agent with a catalyst system in the presence of a flowing carrier gas, to form a mono alkylated dihydroxy aromatic compound, wherein said catalyst system has pores having diameters of 100 to 400 Angstroms.

23. The process of claim 22, wherein said contacting is done at a weighted hourly space velocity of 0.1 to 10.

24. A continuous process comprising:
    contacting a mixture of hydroquinone, monoglyme, water and methanol with a catalyst system in the presence of flowing nitrogen gas, to form 2-methyl hydroquinone, wherein said catalyst system comprising magnesium oxide and copper is obtained by the calcination of a catalyst precursor system, wherein said catalyst precursor system comprises magnesium carbonate, copper and poly ethylene glycol.

25. The process of claim 24, wherein said contacting is done at a weighted hourly space velocity of 0.1 to 10.

26. A polycarbonate comprising subunits derived from the mono alkylaled dihydroxy compound prepared according to claim 1.

27. A polycarbonate produced by melt polymerization of a diphenyl carbonate and a mixture of dihydroxy aromatic compounds comprising a mono alkylated dihydroxy aromatic compound in the presence of a catalyst wherein the mono alkylated dihydroxy compound was prepared by the method of claim 1.

* * * * *